United States Patent
Rehm et al.

(10) Patent No.: US 12,226,586 B2
(45) Date of Patent: Feb. 18, 2025

(54) DRAINAGE SYSTEM AND METHOD

(71) Applicant: C.R. Bard, Inc., Murray Hill, NJ (US)

(72) Inventors: Eric A. Rehm, Lawrenceville, GA (US); Anthony S. Esposito, Jr., Oxford, GA (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 843 days.

(21) Appl. No.: 15/801,639

(22) Filed: Nov. 2, 2017

(65) Prior Publication Data

US 2019/0126006 A1    May 2, 2019

(51) Int. Cl.
*A61M 25/00* (2006.01)
*A61B 10/00* (2006.01)
(Continued)

(52) U.S. Cl.
CPC ....... *A61M 25/0017* (2013.01); *A61B 10/007* (2013.01); *A61F 5/44* (2013.01);
(Continued)

(58) Field of Classification Search
CPC .............. A61M 25/0017; A61M 39/22; A61M 25/0075; A61M 2025/0078; A61M 2205/50; A61M 2205/3334; A61M 2202/0496; A61M 2039/226; A61M 2206/10; A61M 2205/3331; A61M 2230/005; A61M 16/024; A61M 2016/0027; A61M 2205/3327; A61M 2205/3344; A61M 1/1086; A61M 2205/3337; A61M 2005/3123; A61M 25/0082; A61M 5/16877; A61M 5/16881; A61M 5/16886; A61F 5/44; A61F 13/0283; A61F 2013/0296; A61F 2/042; A61B 10/007; A61B 5/4839; A61B 5/0022; A61B 5/14542; A61B 5/4845; A61B 5/4848; A61B 10/0051; A61B 5/0064; A61B 5/0205; A61B 5/024; A61B 5/02416; A61B 5/0806; A61B 5/14551; A61B 5/6801; A61B 5/6816; A61B 5/6823; A61B 5/6826; A61B 5/6829; A61B 5/6898; A61B 5/7203; A61B 5/7405; A61B 5/746; A61B 5/747; A61B 5/748; A61B 7/003; A61B 17/00234; A61B 17/3403; A61B 2017/3413; A61B 2217/005;
(Continued)

(56) References Cited

U.S. PATENT DOCUMENTS 4,556,997 A * 12/1985 Takamiya ............... A61G 5/128
280/304.1
4,810,242 A * 3/1989 Sundblom ............... A61M 1/74
604/28
(Continued)

*Primary Examiner* — Kai H Weng
*Assistant Examiner* — Alessandro R Del Priore
(74) *Attorney, Agent, or Firm* — Rutan & Tucker LLP

(57) ABSTRACT

A drainage system comprising: (a) a catheter including a sensor; (b) a first valve in fluid communication with an interior of the catheter; (c) a controller communicatively coupled to the sensor, the controller including logic configured to direct at least one of opening and closing of the first valve using at least one of an elapsed time and a presence of a predetermined condition; and, (d) a venturi pump in fluid communication with the interior of the catheter.

21 Claims, 2 Drawing Sheets

(51) Int. Cl.
*A61F 5/44* (2006.01)
*A61M 39/22* (2006.01)

(52) U.S. Cl.
CPC ........ *A61M 25/0075* (2013.01); *A61M 39/22* (2013.01); *A61M 2025/0078* (2013.01); *A61M 2039/226* (2013.01); *A61M 2202/0496* (2013.01); *A61M 2205/3334* (2013.01); *A61M 2205/50* (2013.01); *A61M 2206/10* (2013.01)

(58) Field of Classification Search
CPC ... A61B 2560/0214; A61B 5/002; A61B 5/01; A61B 5/087; A61B 10/00; A61B 10/0045; A61B 17/0218; A61B 17/22004; A61B 17/24; A61B 17/3421; A61B 17/3474; A61B 17/8805; A61B 2010/0006; A61B 2010/0009; A61B 2017/00738; A61B 2017/246; A61B 2017/345; A61B 2034/107; A61B 2034/2046; A61B 2034/301; A61B 2050/185; A61B 2503/40; A61B 2560/0219; A61B 2560/04; A61B 2560/0462; A61B 2562/0233; A61B 2562/0247; A61B 2562/0271; A61B 34/10; A61B 34/20; A61B 34/25; A61B 34/32; A61B 34/70; A61B 34/76; A61B 50/13; A61B 50/18; A61B 5/0002; A61B 5/0026; A61B 5/0031; A61B 5/02055; A61B 5/0215; A61B 5/02154; A61B 5/02158; A61B 5/029; A61B 5/03; A61B 5/04286; A61B 5/044; A61B 5/046; A61B 5/04882; A61B 5/05; A61B 5/14539; A61B 5/14546; A61B 5/14557; A61B 5/204; A61B 5/208; A61B 5/4064; A61B 5/4343; A61B 5/4833; A61B 5/6852; A61B 5/6866; A61B 5/7264; A61B 5/742; A61B 8/065; A61B 90/361; G16H 40/63; G16H 10/60; G16H 20/17; G16H 40/67; G16H 20/13; G16H 15/00; G16H 20/10; G16H 20/40; G16H 40/60; G08B 21/0415; G08B 21/0469; G08B 21/0476; G08B 21/0492; G08B 3/10; G08B 5/22; G06F 19/00; G06F 3/04817; G06F 19/3456; G06F 19/3462; G06F 21/31; G06F 3/0482; G06F 3/04847; G06F 3/04883; G06F 3/167; A61J 1/1406; A61J 1/20; A61J 1/2024; F16K 3/03; G06Q 10/087; G06Q 20/10; G06Q 50/22

See application file for complete search history.

(56) References Cited

U.S. PATENT DOCUMENTS

| | | | | |
|---|---|---|---|---|
| 4,880,411 | A | * | 11/1989 | Fangrow, Jr. ......... A61M 39/22 604/149 |
| 5,242,404 | A | * | 9/1993 | Conley ............... A61M 1/0031 604/119 |
| 5,359,233 | A | * | 10/1994 | Mumper ................ H03K 17/22 327/143 |
| RE35,707 | E | * | 12/1997 | Takamiya et al. ..... A61G 5/045 280/304.1 |
| 2007/0005002 | A1 | * | 1/2007 | Millman ................ A61M 1/76 604/30 |
| 2008/0281254 | A1 | * | 11/2008 | Humayun ........... A61F 9/00736 604/22 |
| 2018/0177458 | A1 | * | 6/2018 | Burnett ................. A61B 5/036 |

* cited by examiner

DRAINAGE SYSTEM AND METHOD

RELATED ART

Field of the Invention

The present disclosure is directed to drainage systems and method of operating drainage systems including drainage systems and associated methods for draining contents of a human bladder.

INTRODUCTION TO THE INVENTION

It is a first aspect of the present invention to provide a drainage system comprising: (i) a catheter including a sensor; (ii) a first valve in fluid communication with an interior of the catheter; (iii) a controller communicatively coupled to the sensor, the controller including logic configured to direct at least one of opening and closing of the first valve using at least one of an elapsed time and a presence of a predetermined condition; and, (iv) a venturi pump in fluid communication with the interior of the catheter.

In a more detailed embodiment of the first aspect, the logic is configured to open the first valve when power to the controller is interrupted. In yet another more detailed embodiment, the system further includes at least one of a pump and a compressor configured to supply pressurized fluid to the venturi pump. In a further detailed embodiment, the system further includes at least one of high pressure fluid source configured to supply pressurized fluid to the venturi pump. In still a further detailed embodiment, the controller is communicatively coupled to the first valve to direct at least one of opening and closing of the first valve. In a more detailed embodiment, the logic is configured to iteratively determine whether an elapsed time since the first valve was most recently closed has satisfied a predetermined value and, if so, directing the first valve to open. In a more detailed embodiment, the logic is configured to iteratively determine whether an elapsed time since the first valve was most recently opened has satisfied a predetermined value and, if so, directing the first valve to close. In another more detailed embodiment, the logic is configured to iteratively determine whether a condition monitored by the sensor satisfies a predetermined value and, if so, directing the first valve to open. In yet another more detailed embodiment, the logic is configured to iteratively determine whether a condition monitored by the sensor satisfies a predetermined value and, if so, directing the first valve to close. In still another more detailed embodiment, the logic is configured to determine (a) whether an elapsed time since the first valve was most recently closed has satisfied a first predetermined value and, if so, directing the first valve to open; and, if the elapsed time has not satisfied the first predetermined value, (b) whether a condition monitored by the sensor satisfies a second predetermined value and, if so, directing the first valve to open, and the logic is configured to iteratively determine (a) and (b) until at least one of the elapsed time satisfies the first predetermined value or the condition satisfies the second predetermined value.

In yet another more detailed embodiment of the first aspect, the logic is configured to determine (a) whether an elapsed time since the first valve was most recently opened has satisfied a first predetermined value and, if so, directing the first valve to close; and, if the elapsed time has not satisfied the first predetermined value, (b) whether a condition monitored by the sensor satisfies a second predetermined value and, if so, directing the first valve to close, and the logic is configured to iteratively determine (a) and (b) until at least one of the elapsed time satisfies the first predetermined value or the condition satisfies the second predetermined value. In yet another more detailed embodiment, the logic is configured to determine (a) whether an elapsed time since the first valve was most recently closed has satisfied a first predetermined value and, if so, directing the first valve to open; and, if the elapsed time has not satisfied the first predetermined value, (b) whether a condition monitored by the sensor satisfies a second predetermined value and, if so, directing the first valve to open, the logic is configured to iteratively determine (a) and (b) until at least one of the elapsed time satisfies the first predetermined value or the condition satisfies the second predetermined value, the logic is configured to determine (c) whether an elapsed time since the first valve was most recently opened has satisfied a first predetermined value and, if so, directing the first valve to close; and, if the elapsed time has not satisfied the first predetermined value, (d) whether a condition monitored by the sensor satisfies a second predetermined value and, if so, directing the first valve to close, and the logic is configured to iteratively determine (c) and (d) until at least one of the elapsed time satisfies the first predetermined value or the condition satisfies the second predetermined value. In a further detailed embodiment, the sensor comprises a pressure sensor. In still a further detailed embodiment, the sensor comprises a fluid flow rate sensor. In a more detailed embodiment, the sensor is upstream from the first valve, and the venturi pump is downstream from the first valve. In a more detailed embodiment, the system further includes a sample port in fluid communication with the interior of the catheter. In another more detailed embodiment, the sample port is downstream from the first valve and upstream from the venturi pump. In yet another more detailed embodiment, the system further includes a receptacle in fluid communication with the catheter and configured to receive fluid flowing through the catheter. In still another more detailed embodiment, the receptacle is removably coupled to an outlet of the catheter. In yet another more detailed embodiment, the system further includes a second valve in fluid communication with a high pressure source, the second valve in the open position configured to provides high pressure fluid to the venturi pump, wherein the logic is configured to direct opening of the second valve after closing of the first.

It is a second aspect of the present invention to provide a method of controlling a drainage system comprising (a) a catheter including a sensor, (b) a first valve in fluid communication with an interior of the catheter, (c) a controller communicatively coupled to the sensor, the controller including logic configured to direct at least one of opening and closing of the first valve using at least one of an elapsed time and a presence of a predetermined condition, and (d) a venturi pump in fluid communication with the interior of the catheter, the method comprising: (A) monitoring at least one of: (i) an elapsed time since the first valve was most recently closed, and (ii) a condition using data from the sensor; (B) opening the first valve responsive to at least one of: (i) the elapsed close time satisfying a first predetermined time value, and (ii) the condition satisfying a first predetermined condition value; and, (C) operating the venturi pump when the first valve is closed.

In a more detailed embodiment of the second aspect, the method further includes: (D) monitoring at least one of: (i) an elapsed open time since the first valve was most recently opened, and (ii) the condition using data from the sensor; and, (E) closing the first valve responsive to at least one of:

(i) the elapsed open time satisfying a second predetermined time value, and (ii) the condition satisfying a second predetermined condition value. In yet another more detailed embodiment, the act of monitoring includes monitoring both (i) an elapsed time since the first valve was most recently closed, and (ii) a condition using data from the sensor. In a further detailed embodiment, the act of monitoring occurs iteratively and sequentially. In still a further detailed embodiment, the act of monitoring includes monitoring both (i) an elapsed time since the first valve was most recently opened, and (ii) the condition using data from the sensor. In a more detailed embodiment, the act of monitoring both (i) an elapsed time since the first valve was most recently opened, and (ii) the condition using data from the sensor, occurs iteratively and sequentially.

DETAILED DESCRIPTION

The exemplary embodiments of the present disclosure are described and illustrated below to encompass fluid transfer systems and method of transferring fluid from one reservoir to another reservoir. More specifically, the exemplary embodiments of the present disclosure are described and illustrated below to encompass bodily fluid drainage system and methods of draining accumulated bodily fluids that include, without limitation, draining urine from a bladder using a catheter, a controller, and a fluid pump. Of course, it will be apparent to those of ordinary skill in the art that the embodiments discussed below are exemplary in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention.

Figure 1:
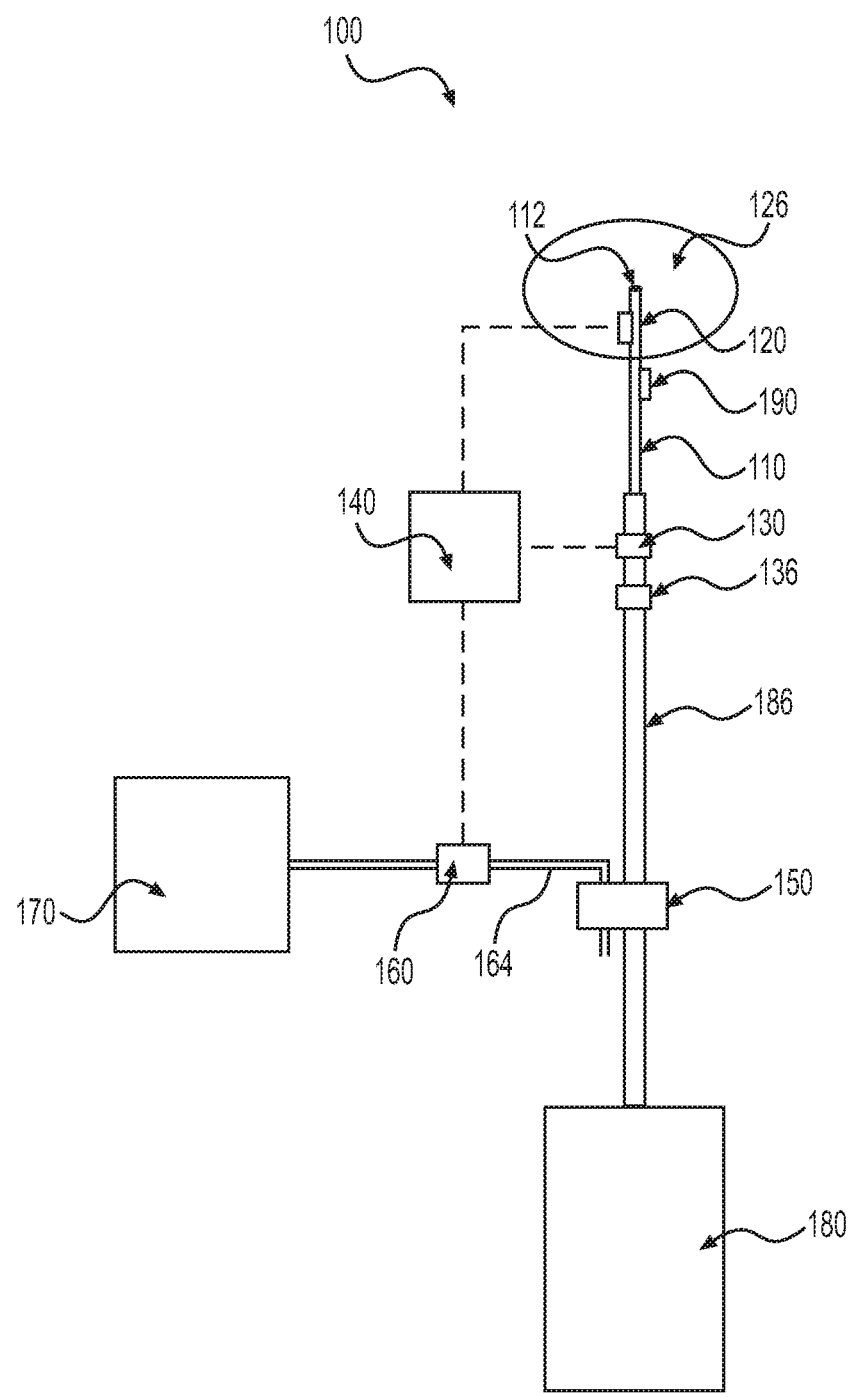
FIG. 1 is a schematic diagram of an exemplary tidal drainage system in accordance with the instant disclosure.

Referring to FIG. 1, an exemplary tidal drainage system 100 provides for the retention/release/drainage of bodily fluids, such as from a bladder, via an intelligent control. In exemplary form, the system 100 may include a catheter 110, a sensor 120 in communication with the inlet 112 of the catheter (presumably in fluid communication with an interior of a patient's bladder 126 when the catheter 110 is inserted through the urethra), a valve 130 in fluid communication with the catheter, a vent 136 downstream of, but close to the valve 130, a drainage tubing 186 in fluid communication with the catheter, and a venturi pump 150 in fluid communication with the catheter located at or near a collection receptacle 180 such as, without limitation, a disposable drainage bag. A controller 140 may be in communication with the valve 130 to command the valve to shut to allow retention of fluid in the body cavity 126 (presumably urine within the patient's bladder) or to open to allow drainage of the fluid from the body cavity. The controller 140 may also be in communication with a fluid valve 160 to command the valve to open to deliver high pressure fluid (from a high pressure fluid source 170) to the venturi pump 150 and cause the venturi pump to operate. The valves 130, 160 may be interlocked either physically or through the controller so that only one valve may be open at a time thus permitting evacuation of only the drainage tubing while isolating the body cavity from the suction generated by the venturi pump. A more detailed discussion of each of the exemplary components follows.

By way of example, the catheter 110 may comprise a Foley catheter available from C. R. Bard, Inc. Alternatively, the catheter 110 may comprise any of a number of flexible tubing that may be inserted into a relatively small or narrow bodily conduit as a predicate to fluid removal. In exemplary form, the catheter 110 may be fabricated from any number of materials including, without limitation, silicone rubber, nylon, polyurethane, polyethylene terephthalate (PET), latex, and thermoplastic elastomers. Those skilled in the art are familiar with catheter tubing and methods of positioning catheter tubing within bodily conduits/lumens and, accordingly, a detailed discussion of the tubing and associated methods of positioning the tubing within a bodily conduit has been omitted in furtherance of brevity.

As discussed previously, the system 100 may include a sensor 120 at or near the catheter inlet 112. In exemplary form, the sensor 120 may comprise a pressure sensor in fluid communication with the open end 112 of the catheter 110, where the open end 112 of the catheter may be configured to be in fluid communication with a bodily fluid receptacle such as, without limitation, a patient bladder 126. Alternatively, or in addition, the sensor 120 may comprise one or more of an optical sensor, a fluid float sensor, a radar sensor, a laser sensor, an ultrasonic sensor, a hydrostatic sensor, a capacitive level sensor, and a magnetic level sensor. In the context of a pressure sensor, the sensor 120 may comprise any pressure sensor (including load cells and strain gauges) sized to be used with the catheter 110 and operative to measure fluid pressure within the catheter or upstream from the catheter inlet 112. Exemplary pressure sensors 120 include, without limitation, piezo-resistive pressure sensors (Silicon Microstructures 5108) mounted onto a printed circuit board (PCB). Regardless of the sensor configuration, the sensor 120 may be communicatively coupled to the controller 140 and provides periodic or continuous data concerning at least one condition upstream from the valve 130. This communicative coupling may be wired or wireless, with one-way (sensor 120 sending signals to the controller 140) or two-way communication between the controller 140 and the sensor 120. To the extent two-way communication is effectuated, this two-way communication may allow the controller 140 to poll or otherwise periodically signal the sensor 120 to send data to the controller. Those skilled in the art are familiar with wired and wireless communicative coupling between a sensor and a controller, thus a more detailed discussion of the communicative connection and optional polling has been omitted in furtherance of brevity.

In exemplary form, the valve 130 may comprise any valve capable of discontinuing or limiting fluid flow. By way of example, the valve 130 may comprise, without limitation, a gate valve, a globe valve, a ball valve, a butterfly valve, a check valve, a disc valve, a diaphragm valve, a needle valve, and a plug valve.

Figure 2:
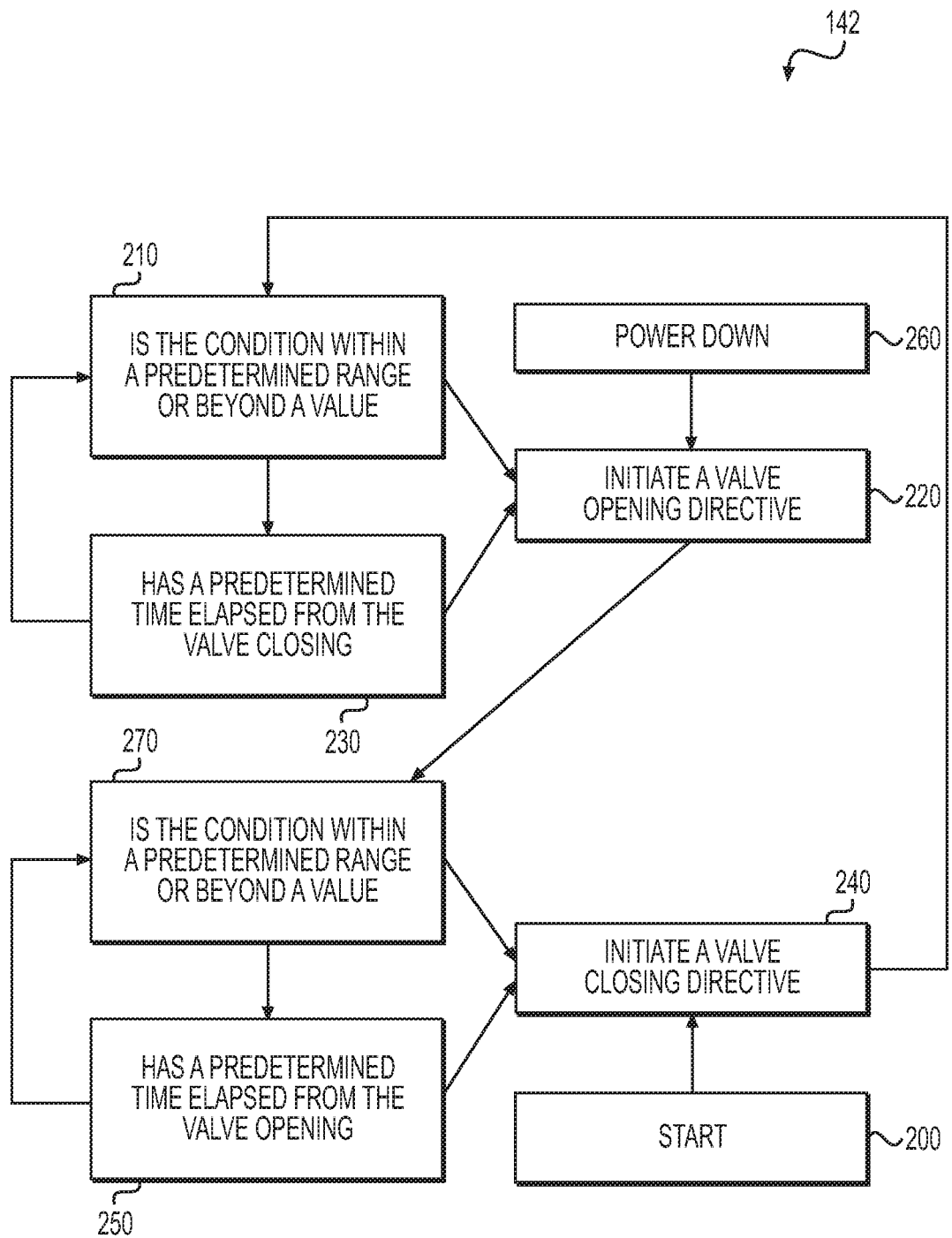
FIG. 2 is a flow diagram of an exemplary logic used by an exemplary controller as part of the exemplary tidal drainage system of FIG. 1

Referring to FIG. 2, the controller 140 may include exemplary logic 142 using information received from the sensor 120 and a clock (not shown) associated with the controller to direct various degrees of opening and closing of the valves 130, 160. The controller may also have the capability to manually actuate valves 130, 160. By way of example, the exemplary controller 140 includes a clock (not shown) providing time data to the controller. In this fashion, the controller 140 may direct the valve 130 to open at a predetermined time and subsequently close at a predetermined time. Opening of the valve 130 allows contents of the bodily reservoir 126 to flow through the catheter 110 and egress into the receptacle 180 via the drainage tubing 186. Conversely, closing of the valve 130 inhibits contents of the bodily reservoir 126, flowing from the catheter 110 and through the drainage tubing 185, from reaching the receptacle 180. In addition to opening or closing the valve 130 on a set timing schedule, or alternatively, per the logic 142, the controller 140 may communicate with the sensor 120 and direct the valve 130 to open if the sensor provides a signal or some other form of data triggering to cause a valve opening sequence. By way of example, if the sensor 120 is a pressure sensor, the controller 140 may receive a signal from the sensor indicative of the pressure upstream from the valve 130 (that may include pressure within the bodily reservoir 126). If the pressure is high enough, indicative of a certain volume of fluid within the bodily reservoir 126, the fluid within the bodily reservoir may need to be partially or totally drained outside of a set time drainage cycle. The following is a discussion of the exemplary logic 142 in accordance with the instant disclosure.

Post inception/initiation 200 of the logic 142, such as when the controller 140 is powered on anew, the controller 140 may poll the sensor 120, periodically receive automated signals/data from the sensor, or continuously receive signals/data from the sensor to gather information as to a condition (e.g., fluid pressure, fluid level, fluid flow, etc.) at the sensor measuring location. Upon the controller 140 receiving data from the sensor 120, the logic 142 utilizes this data to determine at step 210 whether a triggering condition is satisfied. By way of example, the triggering condition for initiating a valve opening directive 220 may be a measured condition being within or outside of a predetermined range (or at, above, or below a predetermined value). By way of example, the predetermined range may be a fluid pressure within the bodily reservoir 126. Alternatively, or in addition, the predetermined value may be a level or amount of fluid within the bodily reservoir 126. Regardless of the condition measured/monitored, if the data is indicative of a value beyond a predetermined range (or is within the predetermined range, or at, above, or below a predetermined value), the logic 142 may proceed to step 220, where the controller 140 initiates a drainage sequence.

Pursuant to the exemplary logic 142, if the monitored or measured condition, for which the sensor 120 sends data concerning, is not within a predetermined range (or at, above, or below a predetermined value), the logic may go on to perform a time determination step 230 to discern whether a predetermined time has elapsed since the valve 130 was most recently closed. By way of the clock, and recording the time the valve 130 is opened and closed that is accessible by the controller 140, the logic 142 uses this recorded data to know the time the valve 130 was most recently closed. By way of example, when the controller 140 is powered on anew, the controller 140 directs the valve 130 to close and it is this starting time that is used as the first valve closing time; otherwise, the valve 130 defaults to an open position if the controller 140 fails or if power/instructions are discontinued to the valve. But, in the context of the valve 130 opening and thereafter being closed, it is the time of this most recent valve closure that is utilized to calculate the time elapsed since the valve most recently closed. In either instance, the controller 140 may be operative to calculate the time elapsed between the valve 130 most recently closing or being closed and the current time of the clock to determine the duration between the current time and the most recent valve closure time. Using this calculated time, the controller 140 compares this elapsed time against a predetermined threshold time to determine if the elapsed time equals or exceeds the predetermined threshold such as, without limitation, twelve hours. If the elapsed time does not meet or exceed the predetermined threshold, the controller 140 reverts to step 210 to determine whether the condition is within a predetermined range (or at, below, or beyond a predetermined value). In a case where the elapsed time equals or exceeds the predetermined value, the controller 140 moves on to step 220 to initiate a drainage sequence.

As part of the drainage sequence, the controller 140 sends one or more signals/data to the valve 130 causing it to open. This valve 130 remains open to allow the bodily reservoir 126 to drain into the receptacle 180 through the catheter 110 and drainage tubing 186. At or near the completion of the drainage sequence, the controller 140 sends one or more signals/data to the valve 130 causing it to shut. Post or concurrent with shutting of the valve 130, the controller 140 sends one or more signals/data to a second valve 160, causing the second valve 160 to open. Opening of the second valve 160 allows high pressure fluid, originating from a high pressure fluid source 170, to reach the venturi pump 150. As those skilled in the art are aware of venturi pumps 150 and the general operation of venturi pumps, a detailed discussion of the operating principles of a venturi pump has been omitted in furtherance of brevity. With the venturi pump 150 operative, by way of the high pressure fluid received through a high pressure conduit 164, and the valve 130 closed, direct fluid communication between the respective ends of the catheter 110 is precluded, but the contents of the drainage tubing 186 downstream of the valve 130 may directed/deposited into the receptacle 180. A vent 136 may be provided that allows ingress of air into the drainage tubing 186 during evacuation. In this circumstance, the venturi pump 150 hastens drainage of the contents of the drainage tubing 186 post closure of the valve 130.

During operation, pressure within the bodily reservoir 126 will be most likely greater than the internal pressure within the catheter 110 and the receptacle 180. In order to hasten drainage from the bodily reservoir 126 or through the catheter 110 itself, the venturi pump 150 is operative to lower the pressure near the outlet of the catheter 110 artificially below ambient pressure, thereby creating a greater driving force to cause fluid flow more rapidly into the receptacle 180 than would be the case if the venturi pump was omitted.

In exemplary form, the second valve 160 may comprise any valve capable of discontinuing or limiting fluid flow. By way of example, the second valve 160 may comprise, without limitation, a gate valve, a globe valve, a ball valve, a butterfly valve, a check valve, a disc valve, a diaphragm valve, a needle valve, and a plug valve.

In exemplary form, the high pressure fluid source 170 may comprise any source of pressurized fluid. By way of example, the high pressure fluid source may comprise, without limitation, a high pressure fluid tank, a compressor, a fluid pump, a conduit downstream from a compressor or pump that can supply high pressure fluid. By way of further example, the high pressure fluid source may include one or more of a hospital high pressure fluid comprising an oxygen source, a nitrogen source, a carbon dioxide source, a nitrous oxide source, a medical air source (with medical air referring to a clean supply of compressed air), and an instrument air source (with instrument air referring to compressed air purified to meet the requirements of the Instrument Society of America and NFPA). It should be noted that if the high pressure source is either a compressor or a fluid pump, the second valve 160 may be omitted and the controller 140 may be configured to selectively power the compressor/pump to deliver high pressure fluid to the venturi pump 150 when needed. Exemplary pressures of the high pressure source may range between ten and fifty psi.

During the drainage sequence, where fluid communication is established between the reservoir 126 and the receptacle 180, the controller 140 may poll the sensor 120, periodically receive automated signals/data from the sensor, or continuously receive signals/data from the sensor to gather information as to a condition (e.g., fluid pressure, fluid level, fluid flow, etc.) at the sensor measuring location. Upon the controller 140 receiving data from the sensor 120, the logic 142 may utilize this data to determine at step 270 if a triggering condition is present to initiate a valve closing directive 240. For example, the controller may determine whether the measured condition is within or outside of a predetermined range (or at, above, or below a predetermined value). By way of example, the predetermined range may be a fluid pressure within the bodily reservoir 126. Alternatively, or in addition, the predetermined value may be a level or amount of fluid within the bodily reservoir 126 or within the receptacle 180 (via the sensor 120 calculating volume from measured flow rate over an elapsed time)). Regardless of the condition measured/monitored, if the data is indicative of triggering condition (a value beyond or within a predetermined range; a value at, above, or below a predetermined value), the logic 142 proceeds to step 240, where the controller 140 initiates a valve closing sequence.

Pursuant to the exemplary logic 142, for example, if the monitored or measured condition, for which the sensor 120 sends data concerning, is not indicative of a triggering condition, the logic may move forward to perform a time determination step 250 to discern whether a predetermined time has elapsed since the valve 130 was most recently opened. By way of the clock, and recording the time the valve 130 is opened and closed, the logic 142 uses recorded data available to the controller 140 to know the time the valve 130 was most recently opened. By way of example, the valve 130 defaults to an open position if the controller 140 fails or if power/instructions are discontinued to the valve. Nevertheless, in the context of the controller 140 being powered on anew, the valve 130 is initially closed so that the system uses the most recent valve opening time (when the controller was powered on anew) to calculate the time elapsed since the valve was most recently opened. In this fashion, the controller 140 determines at step 250 the time elapsed between the valve 130 most recently opening and the current time of the clock to determine the duration between the current time and the most recent valve opening time. Using this calculated time, the controller 140 compares this elapsed time against a predetermined threshold time to determine if the elapsed time equals or exceeds the predetermined threshold such as, without limitation, ten minutes. If the elapsed time does not meet or exceed the predetermined threshold, the controller 140 reverts to step 270 to determine whether the condition is within a predetermined range or beyond a predetermined value. In a case where the elapsed time equals or exceeds the predetermined value, the controller 140 moves on to step 240 to initiate the valve closing sequence.

As part of the valve closing sequence step 240, the controller 140 may send one or more signals/data to the valve 130 causing it to close. At or near the completion of the tubing evacuation cycle, the controller 140 may also send one or more signals/data to a second valve 160, causing the second valve 160 to close. Closing of the second valve 160 discontinues high pressure fluid, originating from the high pressure fluid source 170, from reaching the venturi pump 150. By way of example, the valve 160 may be closed a predetermined time after the valve 130 is closed as a means to draw any residual fluid downstream from the valve 130 into the receptacle 180. Post-closing of both valves 130, 160, the valve closing sequence is complete and the logic may return to step 210 to determine if the condition monitored triggers a valve opening directive 220. Post-closing of both valves 130, 160, if the power is discontinued to the controller 140, the logic moves to a power down step 260 where a valve opening directive is completed to cause only the first valve 130 to be opened. In this manner, if power to the controller is interrupted, fluid may drain from the bodily reservoir 126 and into the receptacle 180 via gravity feed or pressure differential (presuming the pressure within the bodily reservoir is higher than the pressure within the catheter and receptacle 180).

Referring back to FIG. 1, the exemplary tidal drainage system 100 may also include a sample port 190 to allow fluid communication with an interior of the catheter 110. This sample port 190 may be vented and provide access to the interior flow within the catheter for withdrawal of fluid samples and additional monitoring of conditions within the catheter 110 including, without limitation, internal catheter pressure, internal catheter fluid flow rate, and internal catheter fluid temperature. Alternatively, or in addition, the sample port 190 may comprise a quick connect fitting to allow withdrawal of fluid from inside the catheter and into a sample container. In this manner, samples of bodily fluid may be taken at periodic times without requiring removal of the receptacle 180.

Following from the above description and invention summaries, it should be apparent to those of ordinary skill in the art that, while the methods and apparatuses herein described constitute exemplary embodiments of the present invention, the invention contained herein is not limited to this precise embodiment and that changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A drainage system comprising:
a catheter including a sensor;
a first valve in fluid communication with an interior of the catheter;
a controller communicatively coupled to the sensor, the controller including logic configured to direct at least one of opening and closing of the first valve using at least one of an elapsed time and a presence of a predetermined condition sensed by the sensor; and
a venturi pump in selective fluid communication with the interior of the catheter; wherein the first valve is configured to selectively isolate an inlet of the catheter from the venturi pump.

2. The drainage system of claim 1, wherein the logic is configured to open the first valve when power to the controller is interrupted.

3. The drainage system of claim 1, further comprising at least one of a pump and a compressor configured to supply pressurized fluid to the venturi pump.

4. The drainage system of claim 1, further comprising at least one of high pressure fluid source configured to supply pressurized fluid to the venturi pump.

5. The drainage system of claim 1, wherein the controller is communicatively coupled to the first valve to direct at least one of opening and closing of the first valve.

6. The drainage system of claim 1, wherein the logic is configured to iteratively determine whether the elapsed time since the first valve was most recently closed has satisfied a predetermined value and, if so, directing the first valve to open.

7. The drainage system of claim 1, wherein the logic is configured to iteratively determine whether the elapsed time since the first valve was most recently opened has satisfied a predetermined value and, if so, directing the first valve to close.

8. The drainage system of claim 1, wherein the logic is configured to iteratively determine whether a condition monitored by the sensor satisfies a predetermined value and, if so, directing the first valve to open.

9. The drainage system of claim 1, wherein the logic is configured to iteratively determine whether a condition monitored by the sensor satisfies a predetermined value and, if so, directing the first valve to close.

10. The drainage system of claim 1, wherein:
the logic is configured to determine (a) whether the elapsed time since the first valve was most recently closed has satisfied a first predetermined value and, if so, directing the first valve to open; and, if the elapsed time has not satisfied the first predetermined value, (b) whether a condition monitored by the sensor satisfies a second predetermined value and, if so, directing the first valve to open; and
the logic is configured to iteratively determine (a) and (b) until at least one of the elapsed time satisfies the first predetermined value and the condition satisfies the second predetermined value.

11. The drainage system of claim 1, wherein:
the logic is configured to determine (a) whether the elapsed time since the first valve was most recently opened has satisfied a first predetermined value and, if so, directing the first valve to close; and, if the elapsed time has not satisfied the first predetermined value, (b) whether a condition monitored by the sensor satisfies a second predetermined value and, if so, directing the first valve to close; and
the logic is configured to iteratively determine (a) and (b) until at least one of the elapsed time satisfies the first predetermined value and the condition satisfies the second predetermined value.

12. The drainage system of claim 1, wherein:
the logic is configured to determine (a) whether the elapsed time since the first valve was most recently closed has satisfied a first predetermined value and, if so, directing the first valve to open; and, if the elapsed time has not satisfied the first predetermined value, (b) whether a condition monitored by the sensor satisfies a second predetermined value and, if so, directing the first valve to open;
the logic is configured to iteratively determine (a) and (b) until at least one of the elapsed time satisfies the first predetermined value and the condition satisfies the second predetermined value;
the logic is configured to determine (c) whether the elapsed time since the first valve was most recently opened has satisfied the first predetermined value and, if so, directing the first valve to close; and, if the elapsed time has not satisfied the first predetermined value, (d) whether the condition monitored by the sensor satisfies the second predetermined value and, if so, directing the first valve to close; and
the logic is configured to iteratively determine (c) and (d) until at least one of the elapsed time satisfies the first predetermined value and the condition satisfies the second predetermined value.

13. The drainage system of claim 1, wherein the sensor comprises at least one of a pressure sensor and a fluid flow rate sensor.

14. The drainage system of claim 1, wherein:
the sensor is upstream from the first valve; and,
the venturi pump is downstream from the first valve.

15. The drainage system of claim 1, further comprising a sample port in fluid communication with the interior of the catheter.

16. The drainage system of claim 15, wherein the sample port is downstream from the first valve and upstream from the venturi pump.

17. The drainage system of claim 1, further comprising a receptacle in fluid communication with the catheter and configured to receive fluid flowing through the catheter.

18. The drainage system of claim 17, wherein the receptacle is removably coupled to an outlet of the catheter.

19. The drainage system of claim 17, further comprising a second valve in fluid communication with a high pressure source, the second valve in an open position configured to provide high pressure fluid to the venturi pump, wherein the logic is configured to direct opening of the second valve at least one of concurrent with closing the first valve and after closing of the first valve.

20. A method of controlling a drainage system comprising (a) a catheter including a sensor, (b) a first valve in fluid communication with an interior of the catheter, (c) a controller communicatively coupled to the sensor, the controller including logic configured to direct at least one of opening and closing of the first valve using at least one of an elapsed time and a presence of a predetermined condition sensed by the sensor, and (d) a venturi pump in selective fluid communication with an inlet of the catheter via the first valve, the method comprising:
monitoring at least one of: (i) the elapsed time since the first valve was most recently closed, and (ii) a condition using data from the sensor;
opening the first valve responsive to at least one of: (i) an elapsed close time satisfying a first predetermined time value, and (ii) the condition satisfying a first predetermined condition value; and,
operating the venturi pump when the first valve is closed.

21. A drainage system comprising:
a catheter including a sensor;
a first valve in fluid communication with an interior of the catheter;
a controller communicatively coupled to the sensor, the controller including logic configured to direct at least one of opening and closing of the first valve using at least one of an elapsed time and a presence of a predetermined condition; and
a venturi pump in fluid communication with the interior of the catheter;

wherein when the first valve is closed, fluid communication is inhibited between the venturi pump and the interior of the catheter.

* * * * *